(12) United States Patent
Zweymüller

(10) Patent No.: US 6,808,539 B2
(45) Date of Patent: Oct. 26, 2004

(54) LEAFLIKE SHAFT OF A HIP-JOINT PROSTHESIS FOR ANCHORING IN THE FEMUR

(75) Inventor: Karl Zweymüller, Vienna (AT)

(73) Assignee: Plus Endoprothetik AG ( * ) Notice: Subject to any disclaimer, the term of this patent is extended or adjusted under 35 U.S.C. 154(b) by 0 days.

(21) Appl. No.: 10/355,383

(22) Filed: Jan. 30, 2003

(65) Prior Publication Data

US 2003/0120349 A1 Jun. 26, 2003

Related U.S. Application Data

(62) Division of application No. 09/548,166, filed on Apr. 13, 2000, now Pat. No. 6,540,788.

(30) Foreign Application Priority Data

Apr. 13, 1999 (DE) .......................................... 199 16 629
Jun. 23, 1999 (DE) .......................................... 199 28 791

(51) Int. Cl.[7] ................................................. A61F 2/36
(52) U.S. Cl. ................................. 623/23.24; 623/23.35
(58) Field of Search ........................... 623/23.24, 23.35, 623/23.15, 23.18, 23.19, 23.28, 23.26, 23.29, 23.31, 20.36

(56) References Cited

U.S. PATENT DOCUMENTS

| | | | |
|---|---|---|---|
| 3,064,645 A | | 11/1962 | Ficat et al. |
| 4,404,693 A | | 9/1983 | Zweymüller |
| 4,661,112 A | * | 4/1987 | Muller .................... 623/22 |
| 4,664,668 A | | 5/1987 | Beck et al. |
| 4,728,334 A | * | 3/1988 | Spotorno .................... 623/23 |
| 4,813,962 A | | 3/1989 | Deckner et al. |
| 4,908,035 A | | 3/1990 | Deckner et al. |
| 5,133,770 A | | 7/1992 | Zweymüller et al. |
| 5,152,799 A | | 10/1992 | Lyons |
| 5,456,717 A | | 10/1995 | Zweymüller et al. |
| 5,507,833 A | | 4/1996 | Bohn |
| 5,725,586 A | | 3/1998 | Sommerich |
| 5,725,595 A | | 3/1998 | Gustilo |
| 5,928,289 A | * | 7/1999 | Deckner ..................... 623/23 |
| 6,224,634 B1 | | 5/2001 | Keller |
| 6,332,896 B1 | * | 12/2001 | Hubbard et al. ......... 623/23.24 |
| 6,428,578 B2 | * | 8/2002 | White ..................... 623/23.22 |
| 6,540,788 B1 | * | 4/2003 | Zweymuller ............. 623/23.24 |

FOREIGN PATENT DOCUMENTS

| | | |
|---|---|---|
| DE | 23 24 865 | 5/1973 |
| DE | DT 26 27 569 A1 | 12/1977 |
| DE | 87 12607.9 | 9/1987 |
| DE | 38 19 948 | 6/1988 |
| DE | 90 06 893.9 | 6/1990 |
| DE | 41 29 724 A1 | 3/1993 |
| DE | 43 15 143 | 5/1993 |
| DE | 42 23 373 A1 | 1/1994 |
| DE | 94 02 934.2 | 2/1994 |
| DE | G 94 02 934.2 | 10/1994 |
| DE | 295 06 036.0 | 4/1995 |
| DE | 297 05 500 U1 | 9/1998 |
| EP | 0 159 510 B1 | 3/1985 |
| EP | 0 159 510 A2 | 10/1985 |
| EP | 0 159 510 A3 | 3/1987 |
| EP | 0 289 922 A1 | 4/1988 |
| EP | 0 700 670 | 3/1996 |
| EP | 0 821 923 | 7/1997 |
| EP | 1 044 665 A3 | 1/2001 |
| FR | 2 315 902 | 1/1977 |
| FR | 2 681 239 | 9/1991 |
| FR | 2 699 398 | 12/1992 |
| WO | WO 00/59410 | 10/2000 |

\* cited by examiner

*Primary Examiner*—Bruce E Snow
(74) *Attorney, Agent, or Firm*—Knobbe, Martens, Olson & Bear LLP

(57) ABSTRACT

Leaflike shaft (1) of a hip-joint prosthesis for anchoring in the femur, according to a towards a distal end (5) [sic], with a femur-anchoring section (1*a*, . . . 1*i*) having a long axis (A) and with a prosthesis neck (2), wherein the femur-anchoring section 1*a*, . . . 1*i*) has a substantially rectangular external contour in a plane perpendicular to the long axis (A), optionally with recesses in the side edges and/or at the corners.

6 Claims, 5 Drawing Sheets

LEAFLIKE SHAFT OF A HIP-JOINT PROSTHESIS FOR ANCHORING IN THE FEMUR

RELATED APPLICATION

This application is a divisional of U.S. patent application Ser. No. 09/548,166, filed on Apr. 13, 2000 now U.S. Pat. No. 6,540,788.

DESCRIPTION

1. Field of the Invention

The invention relates to a leaflike shaft of a hip-joint prosthesis for anchoring in the femur, with a femur-anchoring section and a prosthesis neck.

Profiled shafts of this kind are generally known. As only a few examples in this regard reference is made to the patents EP 0 427 902 B1 or EP 0 244 610 B1 or U.S. Pat. No. 4,908,035.

As a rule the anchoring section of a shaft of the kind in question here is constructed with smooth surfaces. In EP 0 427 902 B1 it is proposed to construct one section of the shaft with contact surfaces provided with sawteeth. This measure is intended to improve fusion of the shaft to the bony substance.

It is disclosed in the patent CH-A 642 252 that the anterior and posterior leaf surfaces of the leaf part of a shaft are provided with groove-like indentations. However, bone tissue grows poorly into these. The tissue that fills up these indentations is generally a connective tissue with only slight stability.

2. Background of the Invention

The object of the present invention is to configure the femur-anchoring section of a leaflike shaft in such a way that the the tissue growing onto the prosthesis consists to the greatest possible extent of spongy bone tissue, so as to ensure long-term, firm retention of the shaft in the femur.

This object is achieved by a leaflike shaft with the characteristics given in claim 1.

SUMMARY OF CERTAIN INVENTIVE ASPECTS

The invention includes the fundamental idea that the femur-anchoring section of the shaft is substantially rectangular in cross section, so that in simplified (ignoring the tapering toward the tip) terms it is constructed as a "four-edged" profile, in particular as

- oblique-cross profile
- H profile
- double-H or -comb profile
- rectangular hollow profile
- rectangular facet profile
- rectangular notch profile
- approximately trapezoidal profile (with or without recesses at the sides or in the interior)
- or the like.

These profiles all exhibit, to a greater or lesser extent, the property that in the space between the anchoring section of the shaft and the wall of the surgically created cavity spongy bone tissue forms, so that revascularization of the bone occurs. The alternatives in accordance with the invention have the advantage that their periphery comprises substantially four edges, situated at the corners of a rectangle or trapezoid that extends perpendicular to the central axis of the shaft. This basic shape of a shaft has been found in practice to be particularly advantageous for the revascularization of the bone tissue.

It has further been found that a predetermined overdimensioning of the side surfaces of the shaft in comparison to the "rasped" dimension ("null dimension")—with the exception of the edge regions, which should fit precisely—is advantageous in this respect, especially in the proximal section of the shaft.

With the further development in accordance with the invention the revascularization of the bone tissue is additionally promoted, while on one hand the necessary stability or solidity of the shaft is preserved, but on the other hand the intervening space between shaft and operation-cavity wall is enlarged, with the result that a greater amount of new spongiosa is formed.

Advantageous details of the prosthesis shaft in accordance with the invention are presented in the subordinate claims and explained in detail in the following description of exemplary embodiments with reference to the attached drawings, wherein

DETAILED DESCRIPTION OF CERTAIN INVENTIVE EMBODIMENTS

Figure 1:
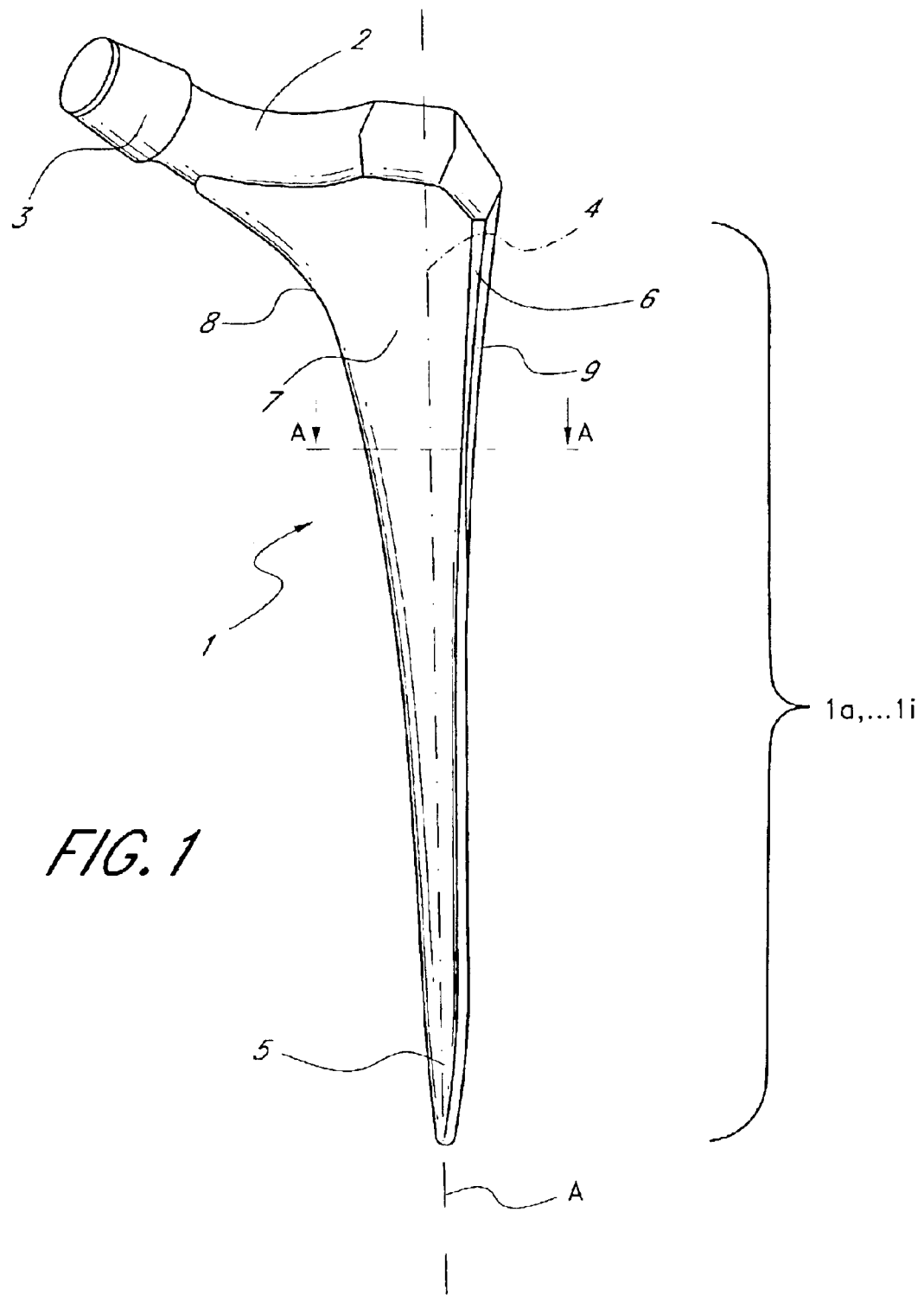
FIG. 1 is a perspective view of a leaflike shaft, the femur-anchoring section of which is further developed in accordance with the invention.

FIG. 1 shows, in perspective, a leaflike shaft 1 of a hip-joint prosthesis for anchoring in the femur. The exemplary embodiment shown here comprises an anchoring section 1a, . . . 1i (see FIGS. 2 to 10), which expands conically on all sides from a distal end 5 to the proximal region, where on the medial side it merges with a continuously curving arch 8. This arch 8 is continuous with a prosthesis neck 2, onto which is set a conically tapering peg 3 which receives a spherical joint head. The prosthesis neck axis intersects the central long axis (not shown in FIG. 1) of the shaft and the anchoring section 1a . . . 1i at an angle that corresponds substantially to the angle between the neck and axis of the femur in a natural hip joint.

Laterally in the proximal region of the shaft 1 a trochanter wing 4 is formed, which is laterally delimited by a side surface 9. The transition between the lateral surface and the posterior or anterior surface is defined by a slanted edge 6 that extends from distal to proximal in the region of the trochanter wing 4. The "leaf" of the shaft 1 is defined in the proximal region and is identified by the reference numeral 7.

In FIGS. 2–10 various cross sections or profile shapes of anchoring sections 1a . . . 1i of the shaft 1 are shown.

Figure 2:
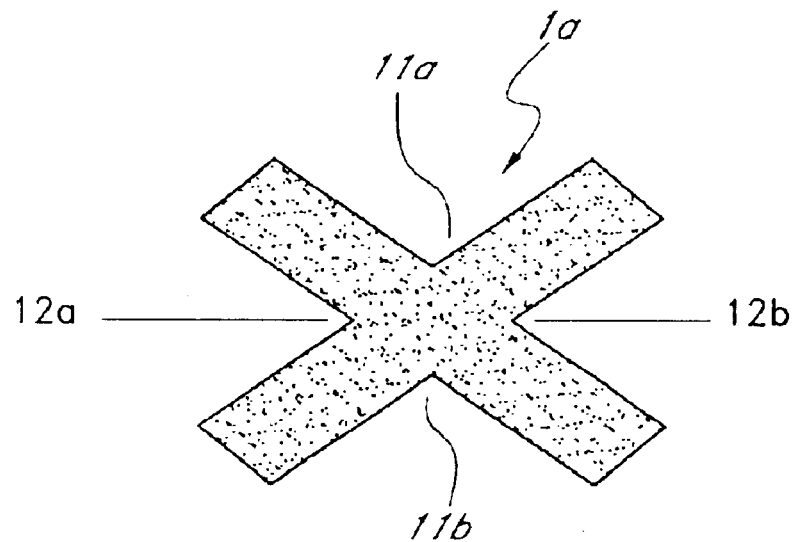
FIGS. 2–9 show various cross sections of the anchoring section of the shaft according to FIG. 1 along the line A—A in FIG. 1.

According to FIG. 2, the anchoring section 1a is constructed as an oblique-cross profile, the limbs of which form V-shaped grooves 11a, 11b on the anterior and posterior aspects respectively, each of which has an angle greater than 90°, and laterally and medially form V-shaped grooves 12a, 12b with an angle smaller than 90°.

Figure 3:
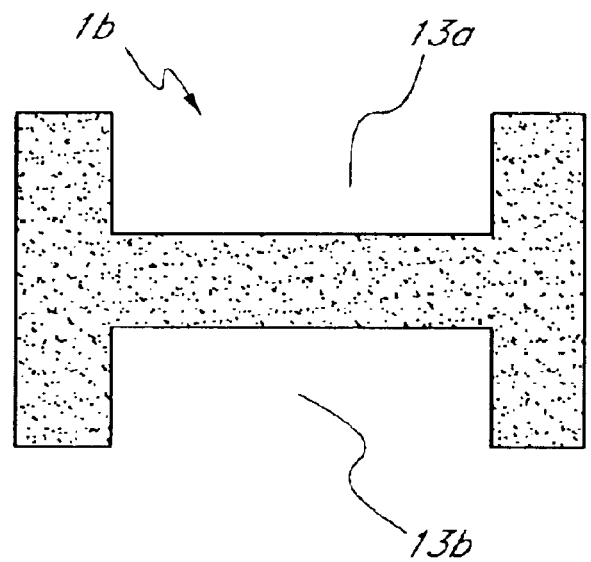

In the embodiment according to FIG. 3 the anchoring section 1b of the shaft 1 is constructed as an H profile. This profile comprises rectangular recesses 13a, 13b on the posterior and the anterior aspect.

Figure 4:
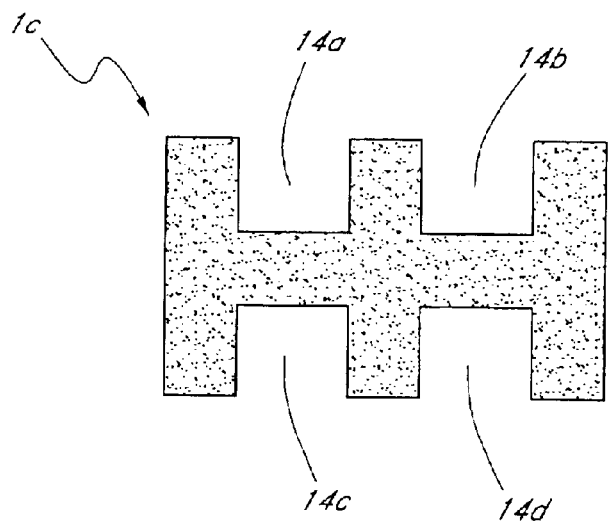

FIG. 4 shows another variant, in which the anchoring section 1c of the shaft 1 is a double-H profile or double-comb profile, in that rectangular longitudinal grooves 14a, 14b, 14c, 14d are formed on the posterior and anterior aspects of the anchoring section.

Figure 5:
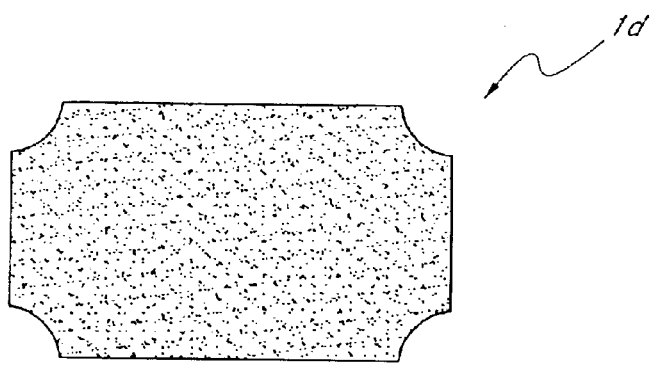

In the variant shown in FIG. 5, the anchoring section 1d of the shaft 1 is roughly rectangular in cross section, with concave facets formed at the four corners.

Figure 6:
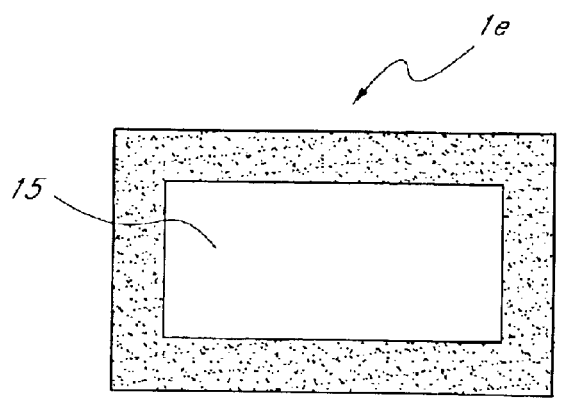
Figure 7:
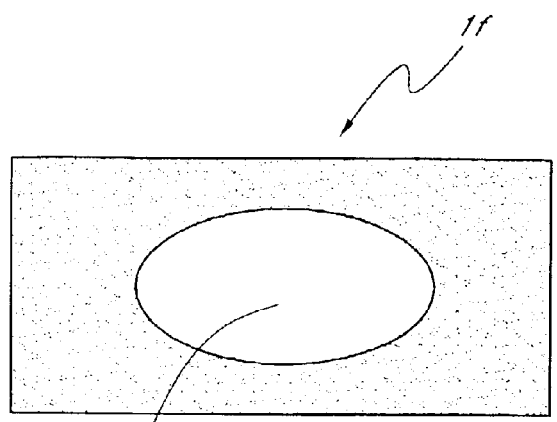

The embodiments according to FIGS. 6 and 7 comprise an anchoring section 1e and 1f, respectively, in the form of a rectangular hollow profile, the embodiment according to FIG. 6 having a cavity 15 that is rectangular in cross section, whereas in the embodiment according to FIG. 7 the cross section of the cavity 16 is elliptical. These two variants are characterized by an especially high stability of the anchoring section, accompanied by low weight.

Figure 8:
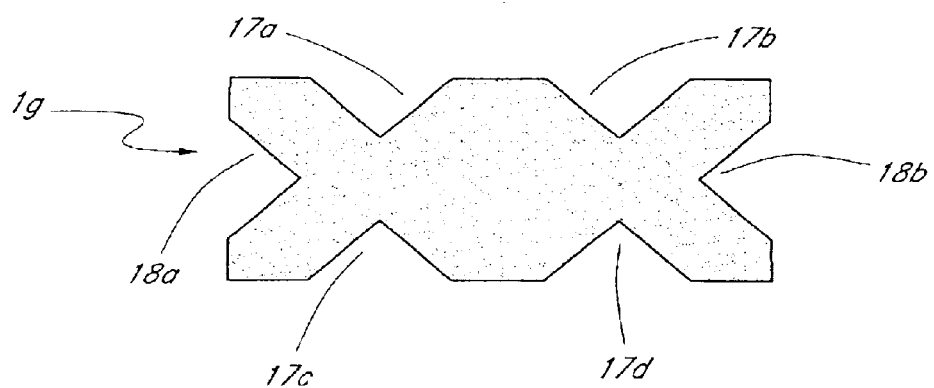

The variant according to FIG. 8 has an anchoring section 1g defined by a rectangular notched profile. On the anterior and on the posterior aspect there are formed two spaced-apart longitudinal notches 17a, 17b and 17c, 17d respectively. Each of these four notches is V-shaped. On the lateral and on the medial aspect one longitudinal notch 18a, 18b is provided, which likewise are V-shaped notches or longitudinal grooves. The corners that delimit the outline of the anchoring section 1g, like those in the embodiment according to FIGS. 6 and 7, can comprise flattened or concave facets like those shown in FIG. 5.

In the embodiment according to FIG. 6 the rectangular cavity 15 can be subdivided by a web or a cross-strut extending in the long direction of the shaft.

The embodiment according to FIG. 8, like that in FIG. 5, can be constructed as a hollow profile with a cavity that extends in the long direction of the shaft and has a circular or oval or elliptical cross section.

Figure 9:
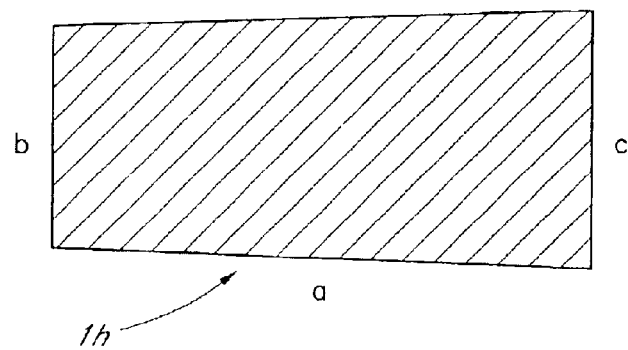

The embodiment of an anchoring section 1h shown in FIG. 9 differs from the embodiments in FIGS. 2–8 in having a trapezoidal cross section, which in this case is symmetrical with two equally long longer sides a in cross section, which correspond to the anterior and posterior surfaces (or faces), and two differently long and parallel shorter sides b, c, of which the shorter one is a medial face and the longer one a lateral face. This symmetrical trapezoidal shape is at present regarded as preferred, but in principle prosthesis shafts with asymmetrical trapezoidal cross sections can also be constructed.

The cross-sectional shapes shown in FIGS. 2–8 (which in those figures are, so to speak, inscribed within a rectangle) can also be modified to give them a basically trapezoidal shape: for instance, an asymmetrical oblique cross, an "H" with a longer and a shorter limb, an embodiment similar to that in FIG. 4 with three differently long limbs, an embodiment corresponding to FIG. 5 but with concave facets in the corner regions of a trapezoidal cross section, or various hollow profiles with a trapezoidal external configuration.

Figure 10:
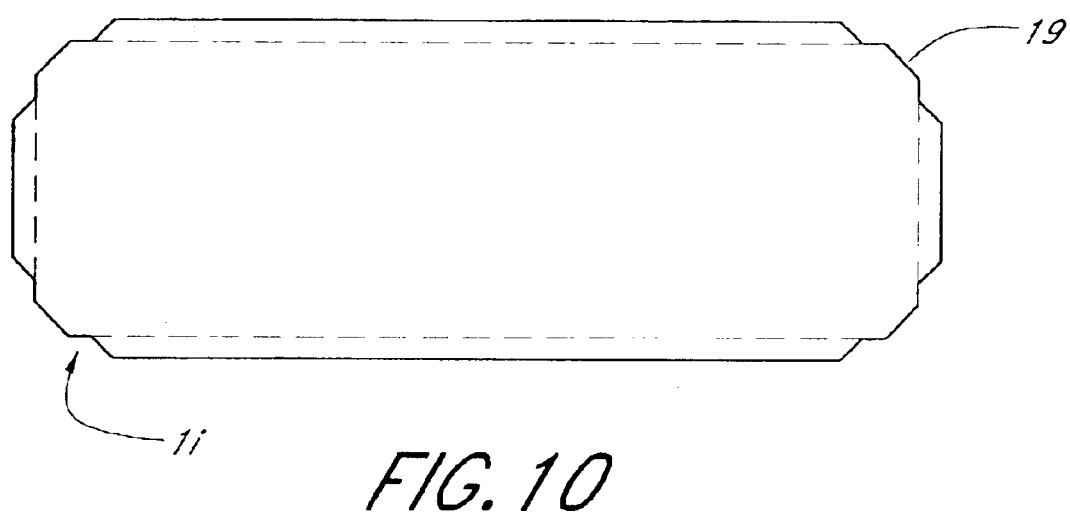
FIG. 10 shows another preferred embodiment in cross section.

In FIG. 10, to illustrate an additional special embodiment of the anchoring section of the shaft prosthesis in accordance with the invention, a cross-sectional shape is shown which again is basically rectangular and at all corners exhibits stepwise chamfered regions 19. The outer contour indicated by the dashed line approximately represents a conventional shaft cross section for the same application, with chamfered regions at an angle of 45° to the side surfaces. It is evident that the proposed new design (indicated by a continuous line) is overdimensioned in comparison with this known embodiment over the greater part of all the side surfaces. However, all the chamfered regions have a middle section, the level of which coincides with the level of chamfering of the corresponding conventional prosthesis shaft. On either side of and parallel to this section are chamfered steps, set back slightly from the middle section.

This embodiment is based on the idea that it is advantageous for a prosthesis shaft—at least in its proximal region—to be overdimensioned by a predetermined amount in comparison to the dimensions of the prepared cavity in the femur (i.e., in comparison to the "rasped dimension"), inasmuch as this overdimensioning increases the pressure of the surfaces against the surrounding bone tissue and thus causes a degree of bone compression. When the ordinary forging precision is also taken into account, the overdimensioning amounts to about 1–3% of the "rasped dimension" in the marrow space, which is also to be understood as the "null dimension".

In the corner regions, by contrast, the fit should be as precise as possible so as not to place the corticalis under excessive stress. Therefore the corner regions are reduced to the exact rasped dimension just prior to implantation. A final shaping to produce the stepped corner configuration shown in FIG. 10 has proved to be relatively easy to accomplish and advantageously effective; in principle, however, other fine structures in the corner region are possible, with which the dimensional conformity of the corners (more precisely: the chamfers) can be made consistent with an overdimensioning of the remaining side and end surfaces—for example, rounding or additional chamfered regions at an angle to the main chamfer.

All the characteristics disclosed in the application documents are claimed as essential to the invention insofar as they are new to the state of the art individually or in combination.

LIST OF REFERENCE NUMERALS

1 Shaft
1a, 1b, 1c, 1d, 1e, 1f, 1g, 1h, 1i Femur-anchoring section
2 Prosthesis neck
3 Peg in form of truncated cone
4 Trochanter wing
5 Distal end
6 Facet
7 Section of the shaft
8 Arch
9 Lateral boundary surface
11a, 11b V-groove
12a, 12b V-groove
13a, 13b Rectangular groove
14a, 14b, 14c, 14d Rectangular groove
15 Rectangular groove
16 Oval cavity
17a, 17b, 17c, 17d, 18a, 18b Longitudinal notch
19 Stepped chamfer
a Long side
b,c End face

What is claimed is:
1. A shaft of a hip-joint prosthesis for anchoring in a femur, comprising:
a prosthesis neck; and
a femur-anchoring section that is connected to the prosthesis neck and that tapers along a longitudinal axis toward a distal end, wherein the femur anchoring section has an anterior face, a posterior face, a lateral face and a medial face, wherein the femur-anchoring section has an external contour in a plane perpendicular to the longitudinal axis having substantially a shape of a trapezoid in which the lateral and medial sides are parallel to one another and are of unequal length, the external contour further comprising concave facets at corner junctions between adjacent pairs of each of the faces.

2. The shaft of claim 1, wherein the shape of the trapezoid is substantially symmetrical such that anterior and posterior side edges of the trapezoid are of equal length and are longer than lateral and medial side edges, wherein the medial side edge is the shortest.

3. The shaft of claim 1, wherein the femur-anchoring section is configured to facilitate revascularization of bone.

4. The shaft of claim 3, wherein the femur-anchoring section comprises cut-outs configured to promote revascularization of spongy bone tissue in the cutout regions.

5. The shaft of claim 1, wherein a first dimension between the anterior and posterior faces and a second dimension between the medial and lateral faces are over-dimensioned relative to corresponding pre-determined rasping dimensions of a femur cavity, and in the regions of the junctions between pairs of adjacent faces, the shaft is sized to be substantially equal to corresponding pre-determined rasping dimensions.

6. The shaft of claim 5, wherein the first and second dimensions are over-dimensioned relative to corresponding pre-determined rasping dimensions by about 1 to 3%.

* * * * *